(12) United States Patent
Wang

(10) Patent No.: US 10,948,612 B1
(45) Date of Patent: Mar. 16, 2021

(54) AUGER PLATE FOR X-RAY PHASE CONTRAST IMAGING AND DETECTORS COMPRISING THE AUGER PLATES

(71) Applicant: Chia Gee Wang, Long Island City, NY (US)

(72) Inventor: Chia Gee Wang, Long Island City, NY (US)

( * ) Notice: Subject to any disclaimer, the term of this patent is extended or adjusted under 35 U.S.C. 154(b) by 0 days.

(21) Appl. No.: 16/712,209

(22) Filed: Dec. 12, 2019

(51) Int. Cl.
*G01T 1/00* (2006.01)
*G01T 1/20* (2006.01)
*A61B 6/00* (2006.01)

(52) U.S. Cl.
CPC .......... *G01T 1/2006* (2013.01); *A61B 6/502* (2013.01)

(58) Field of Classification Search
CPC ............................. G01T 1/2006; A61B 6/502
See application file for complete search history.

(56) References Cited

U.S. PATENT DOCUMENTS

| | | | |
|---|---|---|---|
| 6,099,457 A * | 8/2000 | Good | A61N 5/1027 600/8 |
| 6,429,437 B1 * | 8/2002 | Laugier | G01T 1/20 250/370.09 |
| 2008/0251735 A1 * | 10/2008 | Putterman | H01J 1/30 250/424 |

* cited by examiner

*Primary Examiner* — David P Porta
*Assistant Examiner* — Mamadou Faye
(74) *Attorney, Agent, or Firm* — Ladas & Parry

(57) ABSTRACT

An Auger plate for converting line emission x-ray photons into cascades of Auger electrons that form transient electric charges and for channeling the transient electric charges to an optical imager for conversion of the transient electric charges into a radiographic signal, the Auger plate including an array of Auger sensors which are graphite fibers coated with CsI or Gd coatings. The coatings are configured and arranged to bind the graphite fibers together and to convert the line emission x-ray photons into the cascades of Auger electrons to form the transient electric charges. The graphite fibers are configured and arranged to channel the transient electric charges toward the optical imager. Also, a detector including the Auger plate, a conductive film and an optical imager and a method for preparing the Auger plate.

18 Claims, 4 Drawing Sheets

AUGER PLATE FOR X-RAY PHASE CONTRAST IMAGING AND DETECTORS COMPRISING THE AUGER PLATES

FIELD OF THE INVENTION

The invention is directed to an Auger plate for converting line emission x-ray photons into cascades of Auger electrons that form transient electric charges and for channeling the transient electric charges toward an optical imager for conversion of the transient electric charges into a radiographic signal. The invention is also directed to detectors comprising the Auger plate and a method for preparing the Auger plate.

BACKGROUND OF THE INVENTION

US Patent Application Publication 2018/0078229 to C G Wang and Zhao Cheng (the contents of which are incorporated herein by reference in their entirety) describes Auger mammography using a transmission x-ray tube to provide a largely monochromatic fluorescent line x-ray emission that couples with an Auger sensor imager modified from a CMOS optical imager chip, wherein the metal of the MOS sensor is replaced by an Auger sensor array with a discriminating energy window for Phase Shift Contrast (PSC) imaging, also called X-ray Phase Contrast imaging (XPC). The efficiency of line-emissions coupled with the Auger sensor enhances conventional X-ray Attenuation Contrast (XAC) imaging by two or more orders of magnitude. This allows a higher x-ray beam energy and reduced source/imager distance to reduce the tissue dose by about 200 fold, or 60 fold without breast compression, and the thermal load of the mammo-tube from 6.5 kW to 160 watts without breast compression, which also facilitates the x-ray beam to be delivered from a much sharper e-beam focal point useful for XPC imaging.

The inventor has discovered a way to improve upon the Auger mammography techniques described in the aforementioned patent publication with the use of Auger plates that can be disposed on low cost optical silicon imager chips that are mass fabricated from, for example, 200 mm or 300 mm wafers. The Auger plates can be used with modified optical imager chips and can be mass produced at low cost.

SUMMARY OF THE INVENTION

In accordance with a first embodiment of the invention, there is provided an Auger plate for converting line emission x-ray photons into cascades of Auger electrons that form transient electric charges and for channeling the transient electric charges to an optical imager for conversion of the transient electric charges into a radiographic signal. The plate comprises an army of Auger sensors, the Auger sensors in the array comprise graphite fibers coated with CsI or Gd-caged molecules, wherein the CsI or Gd-caged molecules are configured and arranged to insulate the graphite fibers from one another, to bind the tow of graphite fibers together and to convert the line emission x-ray photons into the cascades of Auger electrons to form the transient electric charges, and wherein the graphite fibers are configured and arranged in the Auger plate to channel the transient electric charges toward an optical imager.

In a preferred aspect of this embodiment, each of the graphite fibers has a diameter between about 1 and 20 microns and the CsI or Gd-caged molecules coating of each fiber has a thickness between about 0.05 and 0.4 microns. Preferably, each of the graphite fibers has a length between about 0.3 and 3 millimeters.

In another embodiment of the invention, there is provided a detection wafer comprising a plurality of the Auger plates. Preferably, the detection wafer is either square or rectangular in shape. For wafers that are square in shape, each side of the square is preferably between about 5 mm and 20 mm in size. In a preferred embodiment, the square wafer is between 200 and 300 cm² in size with each side being about 14.14 or 17.32 cm. For wafers that are rectangular in shape, each long side of the rectangle is preferably between about 17 and 25 mm and each short side of the rectangle is preferably between about 10 and 15 mm. In another preferred embodiment, the rectangular wafer is about 170 or 375 cm² in size with sides of 10 or 15 cm and 17 or 25 cm. In a preferred aspect of this embodiment, the wafer comprises a plurality of the Auger plates.

In yet another embodiment of the invention, there is provided a detector comprising at least one Auger plate and an optical imager comprising a semiconductor collection layer configured for receiving the transient electric charges channeled by the tow of graphite fibers and processing electronics for converting the transient electric charges received in the collection layer into a direct radiographic signal. The detector preferably comprises at least one conductive film covering a plurality of pixels to receive transient electric charges from the Auger plate. The conductive film can comprise, for example, aluminum. A layer of a heavy element can be provided over the conductive film for additional protection for processing electronics from x-ray photons. In one aspect of this embodiment, the heavy element comprises Au or Ta. Preferably, the at least one conductive film has a thickness between about 1 and 3 microns.

In a preferred aspect of this embodiment, the detector comprises a plurality of the Auger plates. In another preferred aspect of this embodiment, the optical imager is a CMOS optical imager chip. In yet another preferred aspect of this embodiment, the optical imager comprises (a) a first image detector wafer comprising a plurality of pixels each of which comprises a photodiode and an imaging circuit and (b) a second wafer of the same size as the first wafer comprising input/output points for power supplies, timing control, a zooming function or a combination thereof, the first and second wafers being disposed in a stacked arrangement one atop the other.

In a still further embodiment of the invention, there is provided a method for preparing an Auger plate, comprising the steps of:

(i) priming a tow of graphite fibers by admixing the graphite fibers with alcohol;

(ii) admixing the primed graphite fibers with CsI or Gd in alcohol and vacuum drying the admixed graphite fibers to form a coating of CsI or Gd on the graphite fibers; and (iii) slicing the tow of graphite fibers coated with CsI or Gd to form the Auger plate. Preferably, the coating of CsI or Gd on the graphite fibers has a thickness of about 0.05 to 0.4 microns.

BRIEF DESCRIPTION OF THE DRAWINGS

FIG. 5A shows the overall imager outline. FIG. 5B shows a standard optical imager before color filters and micro-lens are removed (or not included) to form an optical imager of the invention. FIG. 5C shows a pixel of the optical imager with optical intake area P.

DETAILED DESCRIPTION

Figure 1:
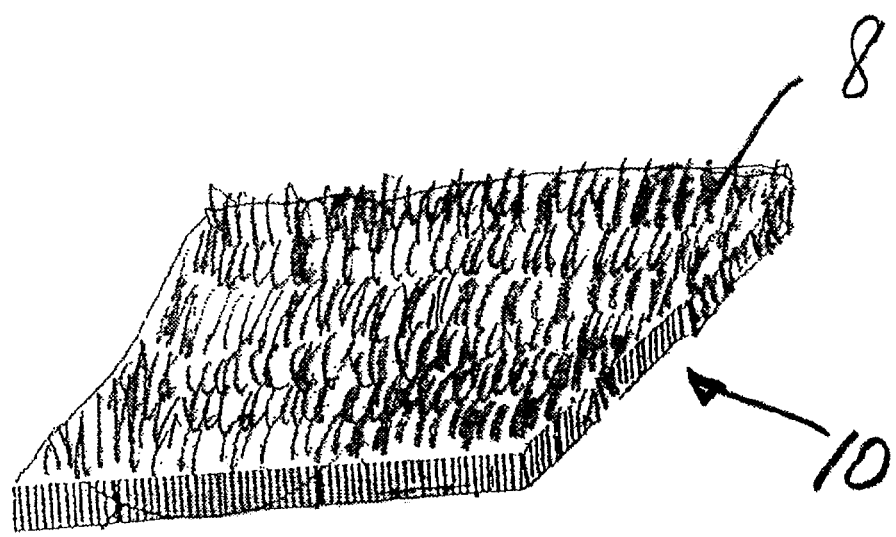
FIG. 1 is a diagrammatic representation of an Auger plate according to the invention comprising a plurality of Auger sensors comprising graphite fibers coated with a CsI or Gd coating.
Figure 2:
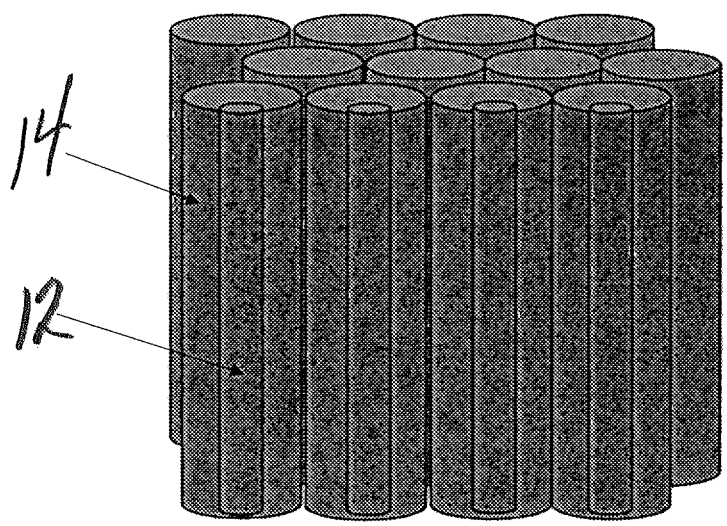
FIG. 2 is a portion of the Auger plate of FIG. 1 in magnified view and in partial cross-section to show the graphite fibers inside the coating.

Referring to FIGS. 1 and 2, an Auger plate 10 according to the invention comprises a plurality of Auger sensors 8. The Auger sensors 8 comprise a tow of graphite fibers 12 coated with a coating 14 of, for example, CsI or Gd-caged molecules. The coating 14 serves to insulate the graphite fibers 12 from each other so that they are unconnected electrically. The coating 14 also serves as a binder for the graphite fibers 12.

Since CsI or Gd-caged molecules can be dissolved in alcohol, the Auger plate 10 can be prepared by priming the graphite fibers with pure alcohol and then treating the primed fibers with alcohol and CsI or caged-Gd molecules. The treated fibers can then be dried by, for example, vacuum pumping to leave the graphite fibers with a CsI or Gd coating. The coating will preferably be between 0.05 and 0.4 microns in thickness, preferably about 0.1 µm. The Auger plate can be sliced from a tow of the coated graphite fibers.

Figure 3:
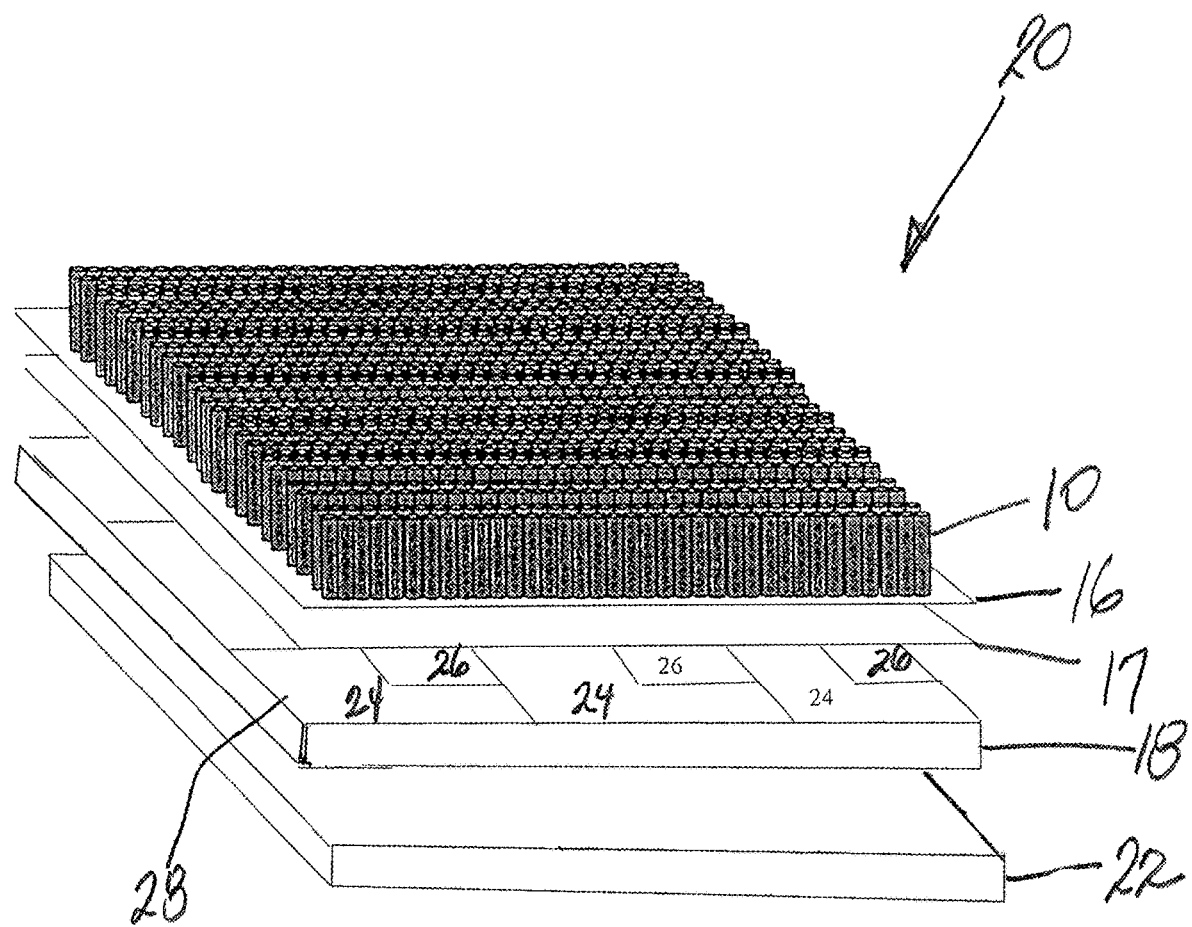
FIG. 3 is a diagrammatic representation of an Auger sensor detector comprising a plurality of Auger plates according to a first embodiment of the invention.

Referring to FIG. 3, there is shown an Auger sensor detector 20 comprising a plurality of Auger plates 10. The Auger plates 10 are positioned on an optional shielding layer 16 which in turn is positioned on a conductive layer or film 17 which in turn is positioned on an optical imager chip 18, which is preferably a silicon chip comprising pixels 28. The optical imager chip 18 is disposed atop an auxiliary chip 22 that can provide I/O points for power supplies, timing control of pixel points and a zooming function, as discussed below.

The Auger plates 10 are configured to channel transient Auger electric charges via the graphite fibers 8 and conductive layer 17 to reach the modified optical pixels 28 beneath and shield them from ionizing x-ray photons. A layer 16 of heavy metal, such as Ta or Au, can be deposited on the aluminum to provide additional shielding if necessary. The conductive film 17 preferably comprises aluminum at a thickness of between 1 and 3 microns. The conductive layer 17 is positioned on the optical imager chip 18, which in a preferred embodiment of the invention comprises a MOS photodiode and a CMOS imaging circuit.

For example, the CMOS optical imaging chip can comprise a conventional Metal-Oxide-Semiconductor (MOS) photodiode 26 and a first-stage Complementary-Metal-Oxide-Semiconductor (CMOS) imaging circuit 24, wherein the photodiode is modified by depositing an array of metal film, such as Ag, I, or AgI, on the oxide as the MOS photodetector metal. This modification is similar to the modification of a CMOS optical imager chip for infrared imaging by replacing color filters with IR filters for IR cameras. The optical imager 18 in Auger sensor detector 20 can use exactly the same logic as in a conventional optical CMOS imager.

In a preferred embodiment of the invention, the input/output (I/O) contacts can be placed at the back of the imager chip 20 in order to have a seamless wafer-sized detector for imaging. An auxiliary chip 22 of the same wafer-size can be provided to complement the imaging detector wafer and to provide I/O points for power supplies, timing control of the pixel points and, most preferably, a zooming function for display in an XAC mode. Preferably, the zoom function will enable, for example, 200 micron points to zoom to subcellular size of 1.6 micron (or 1.4 micron in pixel size). As shown in FIG. 3, the imager chip 18 and auxiliary chip 22 are disposed in a stacked arrangement with one atop the other.

Digital optical imager chips comprising the Auger plates 10, conductive layer 17 and optical imager 18 can be mass produced at low cost from, for example, 200 mm or 300 mm wafers. These detector chips can be modified for x-ray phase contrast (XPC) imaging using Auger sensors of about 200 to 300 mm to form wafer-sized imaging detectors. Using a 200 mm wafer as an example, a wafer could form a square detector of 200 cm² (14.14 cm×14.14 cm), or a rectangular detector of 173.21 cm² (10 cm×17.321 cm). A detector of about 200 cm² in dimension can contain about 200 of the Auger plates 10.

In a preferred embodiment of the invention, the Auger plates can be disposed on the oxide of an MOS photodiode everywhere except at the sensor point P in order to have a nearly 100% fill factor. The remaining area can be covered by a layer of heavy elements such as Ba or Ta in order to protect CMOS circuit elements from x-ray radiation.

Figure 4:
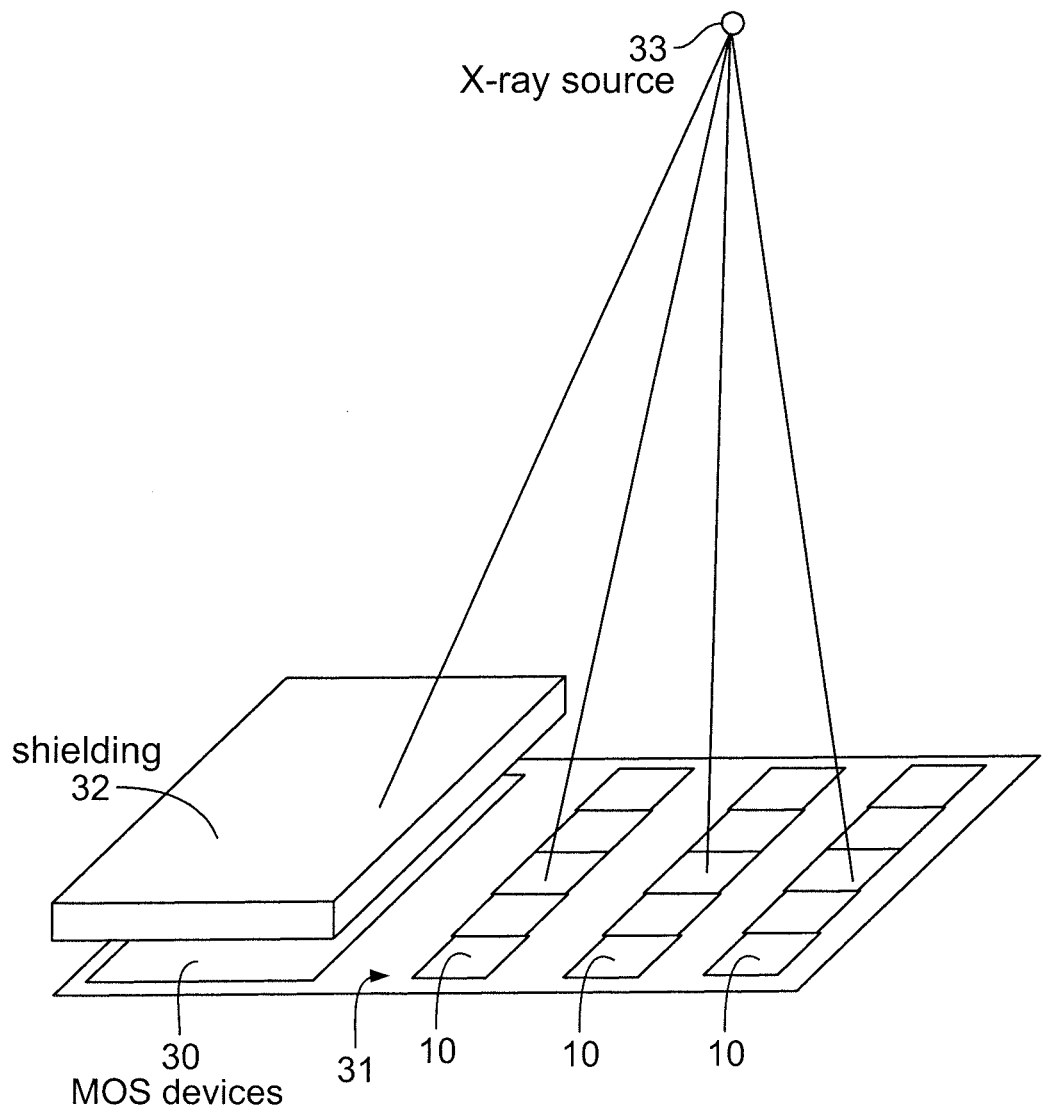
FIG. 4 shows an Auger sensor detector comprising a plurality of Auger plates according to another embodiment of the invention.

Referring to FIG. 4, there is shown another embodiment of the invention, wherein Auger plates 10 are disposed side-by-side with a plurality of MOS devices 30 on a single monolithic substrate 31, as described in US Patent Application Publication 20190179038 (the contents of which are incorporated herein by reference). The single substrate is preferably a semiconductor substrate forming a singular semiconductor chip upon fabrication. The MOS devices may be covered by a shielding layer 32 to shield the MOS devices from radiation from x-ray source 33. The shielding layer can comprise, for example, Ba or Ta.

Figure 5A:
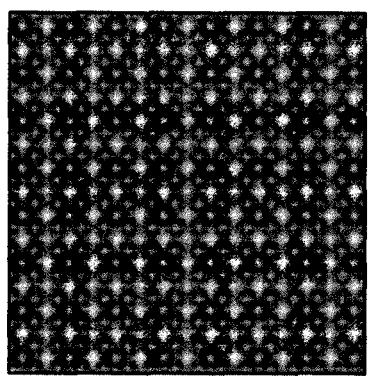
FIGS. 5A-5C shows in sequence how a standard optical imager chip can be modified to arrive at an optical imager chip according to the present invention.
Figure 5B:
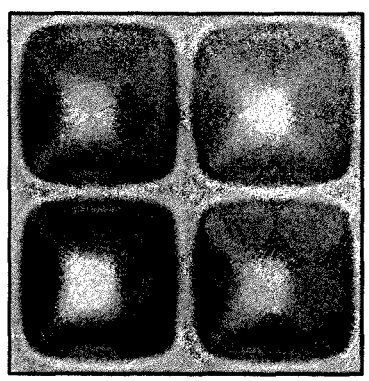
Figure 5C:
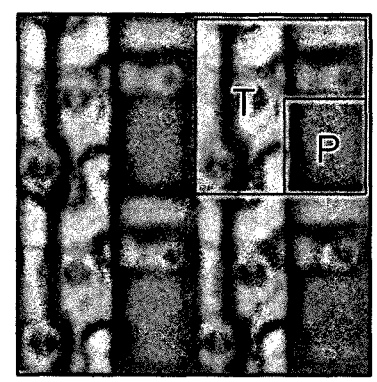

FIGS. 5A-5C show how the optical imager chip 18 can be made by modifying conventional optical imaging chips. FIG. 5A shows the overall imager outline. Input/output (I/O) contacts can be placed at the back of the imager chips in order to have a seamless wafer-sized detector for imaging. A separate chip of the same wafer-size can couple with the imaging chip to handle all the I/O as well as power supplies, memories to provide for image zooming, etc. FIG. 5B shows an imaging pixel array with four colored filters, two of which would typically be green. All of the color filters and micro-lens could be removed (or not included) to form an x-ray Auger detector of the invention. FIG. 5C shows a pixel with optical intake area P having a size of, for example, 0.4 µm. Except for the P area, the pixel can be covered with an oxide followed by an Al film of a few microns that could channel charges to reach P.

The Auger sensor detectors according to the invention may be used in combination with a transmission x-ray tube that provides a largely monochromatic fluorescent line x-ray emission from a lanthanum (La) target to perform Auger mammography in the manner described in US Patent Application Publication 2018/0078229. Using x-ray tubes with a well-defined focal size, which can be evaluated by placing a small metal bead in front of the focal spot and obtaining a much enlarged image of the bead, the edge of the image will exhibit a region of penumbra (partial shadow) that can be measured by a densitometer to determine the size and shape of the focal spot as viewed from the imager.

Figure 6:
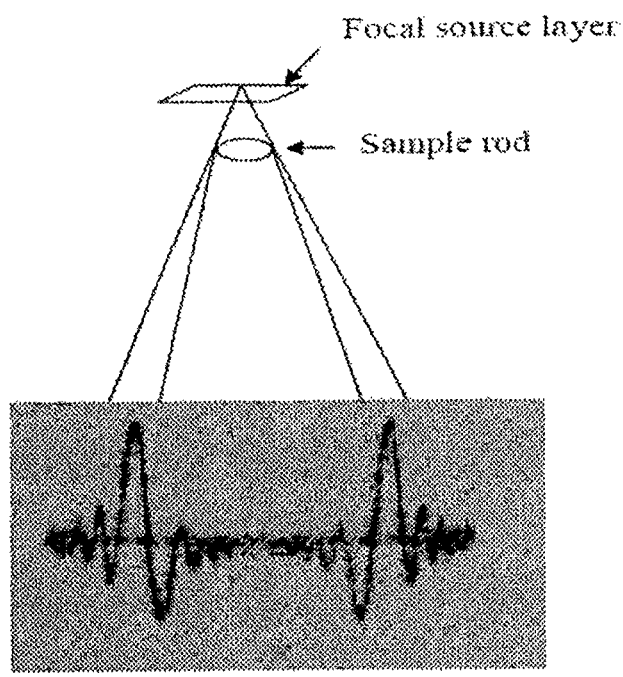
FIG. 6 shows the simulated E-vector of a coherent x-ray photon wave emitting from an x-ray focal spot size a passing over a bead (or a rod, or a heavy atom) and reaching a sensor with distance d from the source.

FIG. 6 shows the simulated oscillating E vector from a penumbral phase interference over a bead or rod or heavy atom. Note that while the E field oscillates between positive and negative, the sensor would register only the total field squared at the sensor point so that for x-ray phase contrast (XPC), the spatial dispersion $\delta_s$ is $$\delta_s \approx \lambda d/a = 0.36 \text{ µm}$$

where $\lambda=1.24$ µm over 34 KeV, and detector-source distance d=40 cm and the focal spot $\alpha$=40 µm. Using a transmission x-ray tube for fluorescent x-ray lines with a line width $\delta_E$ of $\approx 10$ ev gives rise to a temporal dispersion $\delta_t$ of $$\delta_t \approx \lambda E/\delta_E = 0.12 \text{ µm with } E=34 \text{ KeV and } \delta_E=10 \text{ eV}.$$

Similar to a dental x-ray generator, the fluorescent line x-rays from the La target from a transmission x-ray tube will have 34 KeV (La) in resonance with the absorption edge $K_{ab}$ of Cs at 37.8 KeV, and the $K_{ab}$ of 1 at 33.44 KeV, and the brightness-weighted photon energy of La lines become 34.2 KeV. Using 51.47 milliGy for 19.43 grams of CsI at a density of 3.4 g/cm$^3$ covering an area of 200 cm$^2$ over 1 mm in resonance (or soft tissue not in resonance over 10 cm for a dose of 5 milliGy), and for each K-ionization, with 80% probability for 2 Augers and 20% for scintillation with visible photons to be absorbed by black carbon fibers, the Augers per 1.6 µm pixel N (from $8 \times 10^9$ pixels/200 cm$^2$) is $$N = (1000 \text{ erg}/19.43 \text{ g})(1.6 \times 10^{-19})^{-1} \times 2(80\%)/7(34.2 \times 10^3)(8 \times 10^9)$$

$$= 2.7 \times 10^5, \text{ or } 27 \times 10^6 \text{electrons/siemens in ion pulses}.$$

The Auger sensor detectors according to the invention can make use of existing low cost optical chips being mass fabricated from 200 mm or 300 mm wafers with sensor point much larger than the needed dispersion sensor size. The silicon imager chips can be shielded from hard x-rays without blocking the XPC imaging signal. They can also be mass produced at low cost.

Using a transmission x-ray tube to provide hard line x-ray photons and a wafer-sized Auger detector according to the invention, the application to mammography enables the use of a relatively small instrument without involvement of breast compression that delivers sharp cellular density differences with or without tumor-specific heavy molecules such as Gd-caged molecules for diffusion-weighted imaging.

While the invention has been described with respect to a limited number of embodiments, those skilled in the art having benefit of this disclosure will appreciate that other embodiments can be devised which do not depart from the scope of the invention as disclosed herein. Accordingly, the scope of the invention should be limited only by the following claims.

What is claimed is:

1. An Auger plate for converting line emission x-ray photons into cascades of Auger electrons that form transient electric charges and for channeling the transient electric charges to an optical imager for conversion of the transient electric charges into a radiographic signal, the plate comprising an array of Auger sensors, the Auger sensors in the array comprising graphite fibers coated with a coating of CsI or Gd, wherein the CsI or Gd coating is configured and arranged to bind the graphite fibers together and to convert the line emission x-ray photons into the cascades of Auger electrons to form the transient electric charges, and wherein the graphite fibers are configured and arranged to channel the transient electric charges toward the optical imager.

2. The Auger plate according to claim 1, wherein each of the graphite fibers has a diameter between about 1 and 20 microns and the CsI or Gd coating of each fiber has a thickness between about 0.05 and 0.4 microns.

3. The Auger plate according to claim 2, wherein each of the graphite fibers has a length between about 0.3 and 3 mm.

4. The Auger plate according to claim 2, wherein the plate is square in shape with each side of the square being between about 5 mm and 20 mm in size.

5. The Auger plate according to claim 2, wherein the plate is rectangular in shape with each long side of the rectangle being between about 10 and 50 mm and each short side of the rectangle being between about 3 and 30 mm.

6. The Auger plate according to claim 2, wherein the coating comprises CsI.

7. The Auger plate according to claim 2, wherein the coating comprises Gd.

8. A detector comprising the at least one Auger plate according to claim 1 disposed on an aluminum film and an optical imager comprising a semiconductor collection layer configured for receiving the transient electric charges channeled by the graphite fibers via the aluminum film and processing electronics for converting the transient electric charges received in the collection layer into a direct radiographic signal.

9. The detector according to claim 8, further comprising a layer of a heavy element disposed between the Auger plate and the aluminum film for protecting the processing electronics from x-ray photons.

10. The detector according to claim 9, wherein the heavy element comprises Au or Ta.

11. The detector according to claim 7, comprising a plurality of the Auger plates.

12. The detector according to claim 9, wherein the optical imager is a CMOS optical imager.

13. The detector according to claim 8, wherein the layer of Al has a thickness between about 0.05 and 3 microns.

14. The detector according to claim 8, wherein the optical imager comprises (a) a first image detector wafer comprising a plurality of pixels each of which comprises a photodiode and an imaging circuit and (b) a second wafer of the same size as the first wafer comprising input/output points for power supplies, timing control, a zooming function or a combination thereof, the first and second wafers being disposed in a stacked arrangement one atop the other.

15. The detector according to claim 14, wherein the optical imager is a CMOS optical imager.

16. A method for preparing the Auger plate according to claim 1, comprising the steps of:
   (i) priming a tow of graphite fibers by treating the graphite fibers with alcohol;
   (ii) admixing the primed graphite fibers with CsI or Gd and alcohol and vacuum drying the treated graphite fibers to form a coating of CsI or Gd on the graphite fibers; and
   (iii) slicing the tow of graphite fibers coated with the coating of CsI or Gd to form the Auger plate.

17. The method according to claim 16, wherein the coating comprises CsI and has a thickness of about 0.05 to 0.4 microns.

18. The method according to claim 16, wherein the coating comprises Gd and has a thickness of about 0.05 to 0.4 microns.

\* \* \* \* \*